(12) United States Patent
Imamura et al.

(10) Patent No.: US 9,943,224 B2
(45) Date of Patent: Apr. 17, 2018

(54) IMAGE PROCESSING APPARATUS AND IMAGE PROCESSING METHOD

(71) Applicant: CANON KABUSHIKI KAISHA, Tokyo (JP)

(72) Inventors: Hiroshi Imamura, Tokyo (JP); Kazuhiro Miyasa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/137,105

(22) Filed: Apr. 25, 2016

(65) Prior Publication Data

US 2016/0235290 A1 Aug. 18, 2016

Related U.S. Application Data

(63) Continuation of application No. 13/271,604, filed on Oct. 12, 2011, now Pat. No. 9,355,446.

(30) Foreign Application Priority Data

Nov. 19, 2010 (JP) .................................. 2010-259519

(51) Int. Cl.
*G06T 7/00* (2017.01)
*A61B 3/00* (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
CPC .......... G06T 7/0012; G06T 2207/10101; G06T 2207/30041; G06T 2207/202221; G06T 2210/41
(Continued)

(56) References Cited

U.S. PATENT DOCUMENTS

| 7,283,653 B2 | 10/2007 | Zahlmann et al. |
| 7,301,644 B2 | 11/2007 | Knighton et al. |

(Continued)

FOREIGN PATENT DOCUMENTS

| CN | 1717678 A | 1/2006 |
| CN | 101204318 A | 6/2008 |

(Continued)

OTHER PUBLICATIONS

K. Lee, et al., "3-D segmentation of retinal blood vessels in spectral-domain OCT volumes of the optic nerve head," Proceedings of SPIE Medical Imaging 2010, vol. 7626, 2010, pp. 76260V-1 to 76260V-8.

(Continued)

*Primary Examiner* — Rene Towa
(74) *Attorney, Agent, or Firm* — Fitzpatrick, Cella, Harper & Scinto

(57) ABSTRACT

This invention provides an image processing apparatus which allows an operator to easily recognize relevance between morbid portions, which exist in a plurality of layers, according to a disease. An image processing apparatus according to this invention includes an ophthalmic feature acquisition unit which acquires ophthalmic features as anatomical features of the tomogram, a layer designation unit which designates at least two layers required to detect morbid portions corresponding to a disease of a predetermined type from a plurality of layers specified by the ophthalmic features, a morbid portion acquisition unit which detects morbid portions corresponding to the disease of the predetermined type respectively from the layers designated by the layer designation unit, and a composite display unit which generates a composite image by projecting the morbid portions respectively detected from the layers by the morbid (Continued)

portion acquisition unit onto a predetermined two-dimensional image, and displays the composite image.

8 Claims, 10 Drawing Sheets

(51) Int. Cl.
*A61B 3/10* (2006.01)
*A61B 3/12* (2006.01)
*G06K 9/00* (2006.01)
*G06T 11/60* (2006.01)

(52) U.S. Cl.
CPC .............. *A61B 3/12* (2013.01); *G06K 9/0061* (2013.01); *G06T 7/0012* (2013.01); *G06T 11/60* (2013.01); *G06T 2207/10101* (2013.01); *G06T 2207/20221* (2013.01); *G06T 2207/30041* (2013.01); *G06T 2210/41* (2013.01)

(58) Field of Classification Search
USPC .......... 600/558; 382/128, 131; 356/497, 511
See application file for complete search history.

(56) References Cited

U.S. PATENT DOCUMENTS

| | | | |
|---|---|---|---|
| 7,505,142 B2 | 3/2009 | Knighton et al. | |
| 7,659,990 B2 | 2/2010 | Knighton et al. | |
| 7,794,083 B2 | 9/2010 | Tsukada et al. | |
| 7,924,429 B2 | 4/2011 | Knighton et al. | |
| 8,408,704 B2 | 4/2013 | Tomidokoro et al. | |
| 8,474,978 B2 | 7/2013 | Huang et al. | |
| 8,840,248 B2 | 9/2014 | Imamura | |
| 8,861,817 B2 | 10/2014 | Imamura et al. | |
| 9,355,446 B2 | 5/2016 | Imamura et al. | |
| 2004/0102682 A1 | 5/2004 | Zahlmann et al. | |
| 2006/0119858 A1 | 6/2006 | Knighton et al. | |
| 2007/0216909 A1 | 9/2007 | Everett et al. | |
| 2007/0263227 A1 | 11/2007 | Mujat et al. | |
| 2008/0068560 A1 | 3/2008 | Knighton et al. | |
| 2008/0151187 A1 | 6/2008 | Tsukada et al. | |
| 2008/0304733 A1* | 12/2008 | Macaulay | G01N 33/5091 382/133 |
| 2008/0309881 A1 | 12/2008 | Huang et al. | |
| 2009/0180123 A1 | 7/2009 | Knighton et al. | |
| 2010/0194757 A1 | 8/2010 | Tomidokoro et al. | |
| 2010/0202677 A1* | 8/2010 | Imamura | G06T 7/0012 382/131 |
| 2010/0208201 A1 | 8/2010 | Knighton et al. | |
| 2011/0137157 A1 | 6/2011 | Imamura et al. | |
| 2012/0063660 A1 | 3/2012 | Imamura et al. | |
| 2012/0194782 A1 | 8/2012 | Imamura | |

FOREIGN PATENT DOCUMENTS

| | | |
|---|---|---|
| CN | 101778593 A | 7/2010 |
| JP | 2008-154704 A | 7/2008 |
| JP | 2009-066015 A | 4/2009 |
| JP | 2009-089792 A | 4/2009 |

OTHER PUBLICATIONS

Apr. 18, 2012 European Search Report in European Patent Appln. No. 11008270.8.
Robert J. Zawadzki, et al., "Adaptation of a support vector machine algorithm for segmentation and visualization of retinal structures in volumetric optical coherence tomography data sets", Journal of Biomedical Optics, vol. 12, No. 4, Jul./Aug. 2007, pp. 041206-1-041206-8.
Nov. 7, 2013 Chinese Official Action in Chinese Patent Appln. No. 201110376563.7.
Jul. 17, 2014 Chinese Official Action in Chinese Patent Appln. No. 201110376563.7.
Jan. 13, 2015 European Communication in European Patent Appln. No. 11008270.8.
Jul. 22, 2014 Japanese Official Action in Japanese Patent Appln. No. 2010-259519.

* cited by examiner

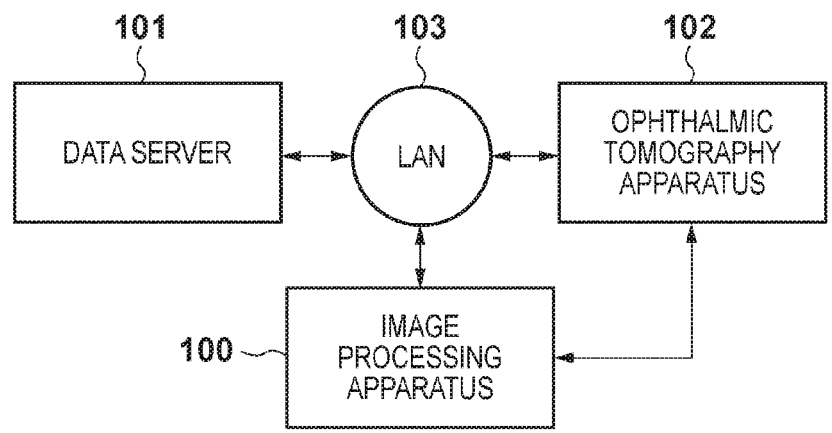
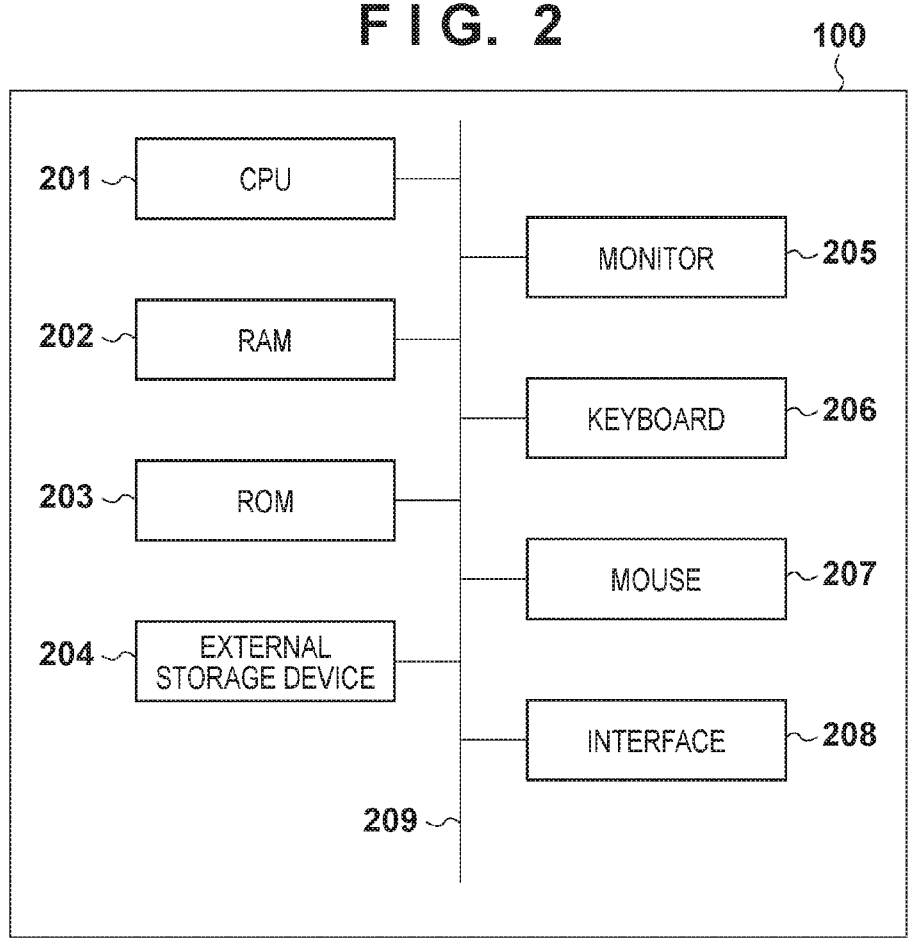

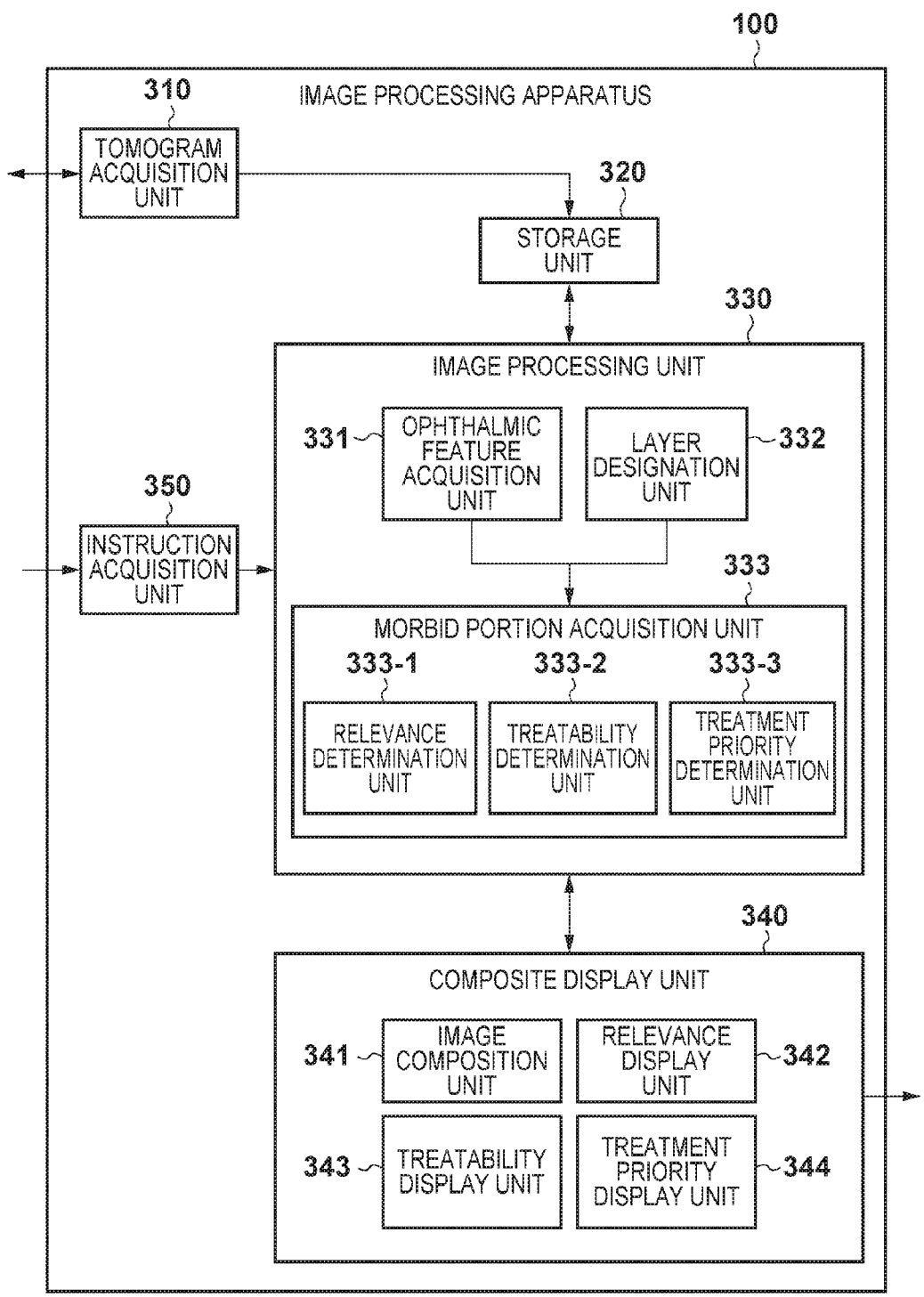

IMAGE PROCESSING APPARATUS AND IMAGE PROCESSING METHOD

This application is a continuation of application Ser. No. 13/271,604 filed Oct. 12, 2011.

BACKGROUND OF THE INVENTION

Field of the Invention

The present invention relates to an image processing technique for processing tomograms.

Description of the Related Art

Conventionally, ophthalmic examinations have been made for the purpose of earlier diagnoses of diseases that come before lifestyle-related diseases and causes of blindness. In general, in such ophthalmic examinations, an ophthalmic tomography apparatus such as an OCT (Optical Coherence Tomography) is used. When such ophthalmic tomography apparatus is used, since it allows to three-dimensionally observe the state of the interior of retina layers, more accurate diagnoses can be given.

Tomograms captured using the ophthalmic tomography apparatus normally undergo image processing in a computer to detect the boundaries of respective layers and blood vessels of a retina, and tissue forms such as the forms of the layers and those of blood vessels are then measured. FIG. 14 shows states in which the boundaries of the layers and blood vessels are detected and tissue forms of an eye portion are measured in various tomograms captured using the ophthalmic tomography apparatus.

An example of 14a of FIG. 14 shows a state in which after an inner limiting membrane B1, inner plexiform layer boundary B4, boundary B5 between inner and outer photoreceptor segments, and retinal pigment epithelium boundary B6 are detected, a retina thickness T1 and GCC (Ganglion Cell Complex) thickness T2 are measured. An example of 14c of FIG. 14 shows a state in which after retinal blood vessels V are detected, the diameters of the retinal blood vessels V are measured.

In this manner, by measuring tissue forms of an eye portion, and comparing whether or not the measurement results (the retina thickness T1, the GCC thickness T2, the diameters of the retinal blood vessels V, and the like) fall within normal value ranges, abnormalities (that is, morbid portions) can be detected.

In some diseases of an eye portion, morbid portions which mutually have deep relevance (primary and associated morbid portions) may separately exist in a plurality of layers. In case of such disease, it is also important to recognize the relevance (distances between the primary and associated morbid portions, the presence/absence and sizes of the associated morbid portions, etc.) between the morbid portions at the time of a diagnosis or treatment plan.

For example, diabetic retinopathy will be described below. 14b of FIG. 14 shows an ophthalmic tomogram of a patient who suffers diabetic retinopathy. As shown in 14b of FIG. 14, in case of diabetic retinopathy, capillaries of retinal blood vessels in retina inner layers become hypertrophic to form microaneurysms MAi (i=1, . . . , n1). Also, some microaneurysms MAi leak plasma components, which are accumulated in retina outer layers. In general, exudative morbid portions formed by accumulating the plasma components in a massive form are called cysts Cj (j=1, . . . , n2).

In case of diabetic retinopathy having such morbid portions, in a treatment, the microaneurysms MAi (primary morbid portions) from which plasma components have leaked out are specified, and are irradiated with a laser beam, thus stopping leakage. At this time, in the vicinity of the microaneurysms MAi from which plasma components have leaked out, associated cysts Cj are often formed, as shown in 14b of FIG. 14, and the leakages of plasma components can be recognized by measuring the sizes of the associated cysts Cj (associated morbid portions).

Therefore, a microaneurysm MAi having a larger cyst Cj at its neighboring position is a primary morbid portion which has a high necessity level of a laser therapy in a treatment plan. However, a portion which has a serious influence on a visual acuity (central fovea F1) and that which has a serious influence on optic nerves (optic papilla) cannot be irradiated with a laser beam. For this reason, upon planning a laser therapy, distances between these portions and leaking points have to be measured so as to confirm whether or not the leaking points are sufficiently separated from these portions.

That is, upon displaying a tomogram, the sizes and positions of the cysts Cj, and the distances between the cysts Cj and the microaneurysms MAi, central fovea F1, and optic papilla can be recognized at a glance, thus expecting to improve the convenience at the time of a diagnosis and treatment plan.

As described above, it is desirable to display the processing result obtained by executing image processing of tomograms captured using the ophthalmic tomography apparatus, so as to allow an operator to easily recognize the relevance of morbid portions for each disease.

On the other hand, various methods for displaying morbid portions detected by executing image processing of tomograms captured using an ophthalmic tomography apparatus have been conventionally proposed.

For example, the specification of U.S. Pat. No. 7,505,142 discloses an arrangement which generates a single projection image by limiting to some layers in a retina, and highlights a retinal blood vessel. Also, Japanese Patent Laid-Open No. 2009-89792 discloses an arrangement which compares and displays form abnormalities (thinning) at a plurality of points along a direction in which a retina nerve fiber travels.

However, the arrangement described in the specification of U.S. Pat. No. 7,505,142 generates a single projection image in some layers, and that described in Japanese Patent Laid-Open No. 2009-89792 displays a single layer. That is, these arrangements do not display morbid portions which separately exist in a plurality of layers in consideration of their relevance, and display modes of these arrangements are not suited to give a diagnosis or make a treatment plan for morbid portions for which their relevance across a plurality of layers has to be recognized.

SUMMARY OF THE INVENTION

The present invention has been made in consideration of the above problems.

An image processing apparatus according to the present invention comprises the following arrangement. That is, an image processing apparatus for executing image processing of a tomogram of an eye portion, comprising: an ophthalmic feature acquisition unit configured to acquire ophthalmic features as anatomical features of the tomogram; a designation unit configured to designate at least two layers required to detect morbid portions corresponding to a disease of a predetermined type from a plurality of layers specified by the ophthalmic features acquired by the ophthalmic feature acquisition unit; a morbid portion acquisition unit configured to detect morbid portions corresponding to the disease of the predetermined type respectively from the layers designated by the designation unit; a generation unit configured to generate a composite image by projecting the morbid portions respectively detected from the layers by the morbid portion acquisition unit onto a predetermined two-dimensional image; and a display unit configured to display the composite image generated by the generation unit.

According to the present invention, the image processing apparatus, which executes image processing of tomograms, allows an operator to easily recognize the relevance between morbid portions which exist in a plurality of layers.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1 is a block diagram showing an example of an image processing system which includes an image processing apparatus 100 according to the first embodiment of the present invention;

FIG. 2 is a block diagram showing the hardware arrangement of the image processing apparatus 100;

FIG. 3 is a block diagram showing the functional arrangement of the image processing apparatus 100;

DESCRIPTION OF THE EMBODIMENTS

Figure 4:
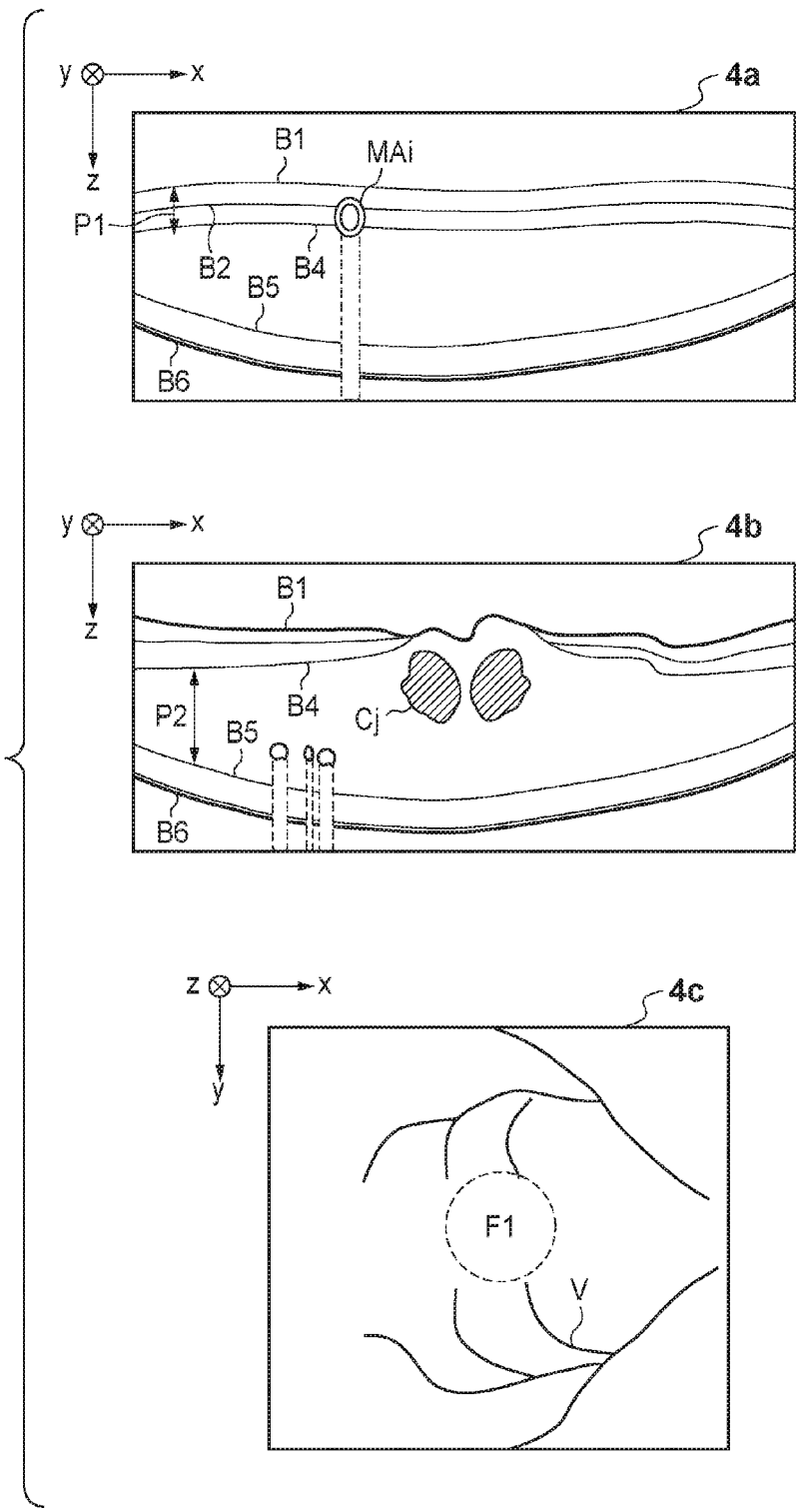
FIG. 4 shows examples of ophthalmic tomograms used upon execution of an image processing function of the image processing apparatus 100.

Embodiments of the present invention will now be described in detail in accordance with the accompanying drawings.

First Embodiment

An overview of an image processing apparatus according to this embodiment will be described first. The image processing apparatus according to this embodiment is characterized by designating, in an ophthalmic tomogram of a patient who suffers diabetic retinopathy, layers (retina inner and outer layers) required to detect morbid portions corresponding to that disease (diabetic retinopathy).

The image processing apparatus is also characterized in that microaneurysms are detected as primary morbid portions from the retina inner layers of the designated layers, cysts are detected as associated morbid portions from the retina outer layers, and these morbid portions are projected onto a predetermined fundus image together with ophthalmic features, thereby displaying them as a composite image.

With this arrangement, the operator can easily recognize the presence/absence of leakage of plasma components from the microaneurysms, the advisability of treatments for the primary morbid portions, the priority levels of treatments for the primary morbid portions, and the like. This embodiment having these characteristic features will be described in detail below.

Note that anatomically, layers from an inner limiting membrane B1 to an inner granular layer (not shown) are defined as the retina inner layers, and those from an outer plexiform layer (not shown) to a retinal pigment epithelium layer B are defined as the retina outer layers. However, on an actual ophthalmic tomogram, since an inner plexiform layer boundary B4 which is slightly located on the inner layer side of the outer plexiform layer can be more accurately detected, layers from the inner limiting membrane B1 to the inner plexiform layer boundary B4 are described as the retina inner layers, and the retina outer layers are described as regions other than the retina inner layers in the retina in this embodiment. Of course, this embodiment can also be practiced by defining the retina inner and outer layers according to the anatomical definitions (after detection of the outer plexiform layer boundary (not shown)).

<1. Arrangement of Image Processing System>

FIG. 1 is a block diagram showing an example of an image processing system including an image processing apparatus 100 according to this embodiment.

As shown in FIG. 1, the image processing apparatus 100 and an ophthalmic tomography apparatus 102 are connected via an optical fiber and interface such as USB or IEEE1394. A data server 101 is connected to the image processing apparatus 100 and ophthalmic tomography apparatus 102 via a LAN (Local Area Network) 103 such as Ethernet®. Note that these apparatus may be connected via an external network such as the Internet.

The ophthalmic tomography apparatus 102 is an apparatus for capturing ophthalmic tomograms, and is, for example, a time-domain or Fourier-domain OCT. The ophthalmic tomography apparatus 102 three-dimensionally captures a tomogram of an eye to be examined (not shown) in response to an operation of an operator (not shown). The captured tomogram is transmitted to the image processing apparatus 100.

The data server 101 holds tomograms of an eye to be examined, ophthalmic features of the eye to be examined (anatomical features acquired from ophthalmic tomograms), normal value data of the ophthalmic features, and the like. The data server 101 holds tomograms of an eye to be examined output from the ophthalmic tomography apparatus 102 and ophthalmic features output from the image processing apparatus 100. Also, in response to a request from the image processing apparatus 100, the data server 101 transmits data (tomograms and ophthalmic features) associated with an eye to be examined, and normal value data of the ophthalmic features to the image processing apparatus 100.

<2. Hardware Arrangement of Image Processing Apparatus 100>

The hardware arrangement of the image processing apparatus 100 will be described below with reference to FIG. 2. Referring to FIG. 2, reference numeral 201 denotes a central processing unit (CPU); 202, a memory (RAM); 203, a control memory (ROM); 204, an external storage device; 205, a monitor; 206, a keyboard; 207, a mouse; and 208, an interface. The external storage device 204 stores a control program required to implement an image processing function according to this embodiment, and data used upon execution of the control program. The control program and data are loaded onto the RAM 202 via a bus 209 under the control of the CPU 201, and are executed by the CPU 201.

<3. Functional Arrangement of Image Processing Apparatus 100>

The functional arrangement of the image processing apparatus 100, which is required to implement the image processing function according to this embodiment, will be described below with reference to FIGS. 3 and 4. FIG. 3 shows the functional arrangement associated with the image processing function of the image processing apparatus 100, and FIG. 4 shows an example of an ophthalmic tomogram used upon execution of the image processing function of the image processing apparatus 100.

As shown in FIG. 3, the image processing apparatus 100 includes a tomogram acquisition unit 310, storage unit 320, image processing unit 330, composite display unit 340, and instruction acquisition unit 350.

The image processing unit 330 further includes an ophthalmic feature acquisition unit 331, layer designation unit 332, and morbid portion acquisition unit 333. The morbid portion acquisition unit 333 further includes a relevance determination unit 333-1, treatability determination unit 333-2, and treatment priority determination unit 333-3.

The composite display unit 340 further includes an image composition unit 341, relevance display unit 342, treatability display unit 343, and treatment priority display unit 344.

The respective functional blocks which configure the image processing apparatus 100 will be described in detail below.

(1) Tomogram Acquisition Unit 310

The tomogram acquisition unit 310 transmits a tomogram acquisition request to the ophthalmic tomography apparatus 102. The tomogram acquisition unit 310 receives a tomogram transmitted from the ophthalmic tomography apparatus 102 via the LAN 103 in response to this acquisition request, and stores it in the storage unit 320.

(2) Ophthalmic Feature Acquisition Unit 331

The ophthalmic feature acquisition unit 331 extracts, as ophthalmic features, an inner limiting membrane, optic nerve fiber layer boundary, ganglion cell layer boundary, inner plexiform layer boundary, outer plexiform layer boundary, boundary between inner and outer photoreceptor segments, retinal pigment epithelium boundary, optic papilla, and central fovea from the tomogram stored in the storage unit 320. Then, the ophthalmic feature acquisition unit 331 acquires an inner limiting membrane B1, inner plexiform layer boundary B4, boundary B5 between inner and outer photoreceptor segments, retinal pigment epithelium boundary B6, and central fovea F1 from the extracted ophthalmic features, as shown in FIG. 4. Also, the ophthalmic feature acquisition unit 331 stores the acquired ophthalmic features in the storage unit 320.

The ophthalmic feature extraction sequence by the ophthalmic feature acquisition unit 331 will be practically described below. The extraction sequence for extracting layer boundaries will be described first. Note that a three-dimensional tomogram to be processed is considered as a set of two-dimensional tomograms (B-scan images), and the following processing is applied to respective two-dimensional tomograms.

A two-dimensional tomogram of interest undergoes smoothing processing to remove noise components. Next, edge components are detected from the two-dimensional tomogram, and some line segments are extracted as candidates of layer boundaries based on their connectivity.

Then, from the extracted candidates, the uppermost line segment is extracted as the inner limiting membrane B1, the second uppermost line segment is extracted as the nerve fiber layer boundary B2, and the third uppermost line segment is extracted as the inner plexiform layer boundary B4. Also, the line segment, which is located on the outer layer side (the larger z-coordinate side in 4a of FIG. 4) of the inner limiting membrane B1 and has a maximum contrast, is extracted as the boundary B5 between inner and outer photoreceptor segments. Furthermore, the lowermost line segment of the layer boundary candidates is extracted as the retinal pigment epithelium boundary B6.

Note that layer boundaries may be precisely extracted by applying a deformable model such as Snakes or a level-set method to have these line segments as initial values. Also, layer boundaries may be detected by a graph cut method.

Note that boundary extraction using a deformable model or the graph cut method may be three-dimensionally executed for a three-dimensional tomogram, or may be two-dimensionally executed for respective two-dimensional tomograms. Also, arbitrary layer boundary extraction methods may be used as long as they can extract layer boundaries from an ophthalmic tomogram.

After the layer boundaries are extracted from the ophthalmic tomogram, two recessed portions are further detected from the form of the extracted inner limiting membrane B1 in descending order of recess depth, thereby extracting the optic papilla (not shown) and central fovea F1. In this case, a shallower recessed portion is extracted as the central fovea F1, and a deeper recessed portion is extracted as the optic papilla.

(3) Layer Designation Unit 332

The layer designation unit 332 decides the types of layers designated to detect principal and associated morbid portions corresponding to a predetermined disease from the ophthalmic tomogram. The types of layers designated to detect morbid portions are decided depending on the type of disease to be diagnosed. In case of this embodiment, since a disease to be diagnosed is diabetic retinopathy, primary morbid portions are microaneurysms, and associated morbid portions are cysts, retina inner layers (P1 in 4a of FIG. 4) including retinal blood vessels V are designated as the type of layer required to detect microaneurysms MAi. Also, as the type of layer required to detect cysts Cj, retina outer layers (P2 in 4b of FIG. 4) where leaked plasma components have accumulated are designated. Assume that layers including the retina inner layers P1 and retina outer layers P2 are specified in advance based on the ophthalmic features acquired by the ophthalmic feature acquisition unit 331.

(4) Morbid Portion Acquisition Unit 333

The morbid portion acquisition unit 333 detects primary and associated morbid portions based on position information of the ophthalmic features acquired by the ophthalmic feature acquisition unit 331 and information of the types of layers designated by the layer designation unit 332.

More specifically, the morbid portion acquisition unit 333 detects the retinal blood vessels V from the retina inner layers designated by the layer designation unit 332, and compares the diameters of the detected retinal blood vessels V with a normal value, thereby detecting the microaneurysms MAi as the primary morbid portions. Furthermore, the morbid portion acquisition unit 333 detects the cysts Cj as the associated morbid portions from the retina outer layers designated by the layer designation unit 332.

Furthermore, the relevance determination unit 333-1 of the morbid portion acquisition unit 333 determines relevance between the morbid portions based on the distances between the detected microaneurysms MAi and cysts Cj, thereby determining treatment necessity levels. Moreover, the treatability determination unit 333-2 of the morbid portion acquisition unit 333 determines the advisability of treatments for the microaneurysms MAi based on the distances between the microaneurysms MAi and central fovea F1. Also, the treatment priority determination unit 333-3 of the morbid portion acquisition unit 333 sets treatment priority values for the respective microaneurysms MAi based on the sizes of the cysts Cj each having a shortest distance to the corresponding microaneurysm MAi. Note that details of these processes by the morbid portion acquisition unit 333 will be described later.

(5) Composite Display Unit 340

The composite display unit 340 generates a composite image for the tomogram using the distributions of the retinal blood vessels V and microaneurysms MAi, the distribution of the cysts Cj, treatment necessity level information, treatment advisability information, and treatment priority values, which are detected by the morbid portion acquisition unit 333. Note that details of the composite image generation processing will be described later.

(6) Instruction Acquisition Unit 350

The instruction acquisition unit 350 acquires an image processing start instruction in the image processing apparatus 100, a save instruction required to save the image processing results of the eye to be examined in the data server 101, and an end instruction required to end the image processing by the image processing apparatus 100. The operator inputs these instructions via, for example, the keyboard 206 and mouse 207.

Note that when the save instruction is issued, the image processing unit 330 and composite display unit 340 transmit a date and time of examination, information required to identify the eye to be examined, tomograms, ophthalmic features, and composite images to the data server 101 in association with each other.

<4. Sequence of Image Processing in Image Processing Apparatus 100>

The sequence of the image processing in the image processing apparatus 100 will be described below with reference to FIGS. 5 to 7. The image processing apparatus 100 starts the image processing shown in FIG. 5 when the instruction acquisition unit 350 acquires an image processing start instruction.

Figure 5:
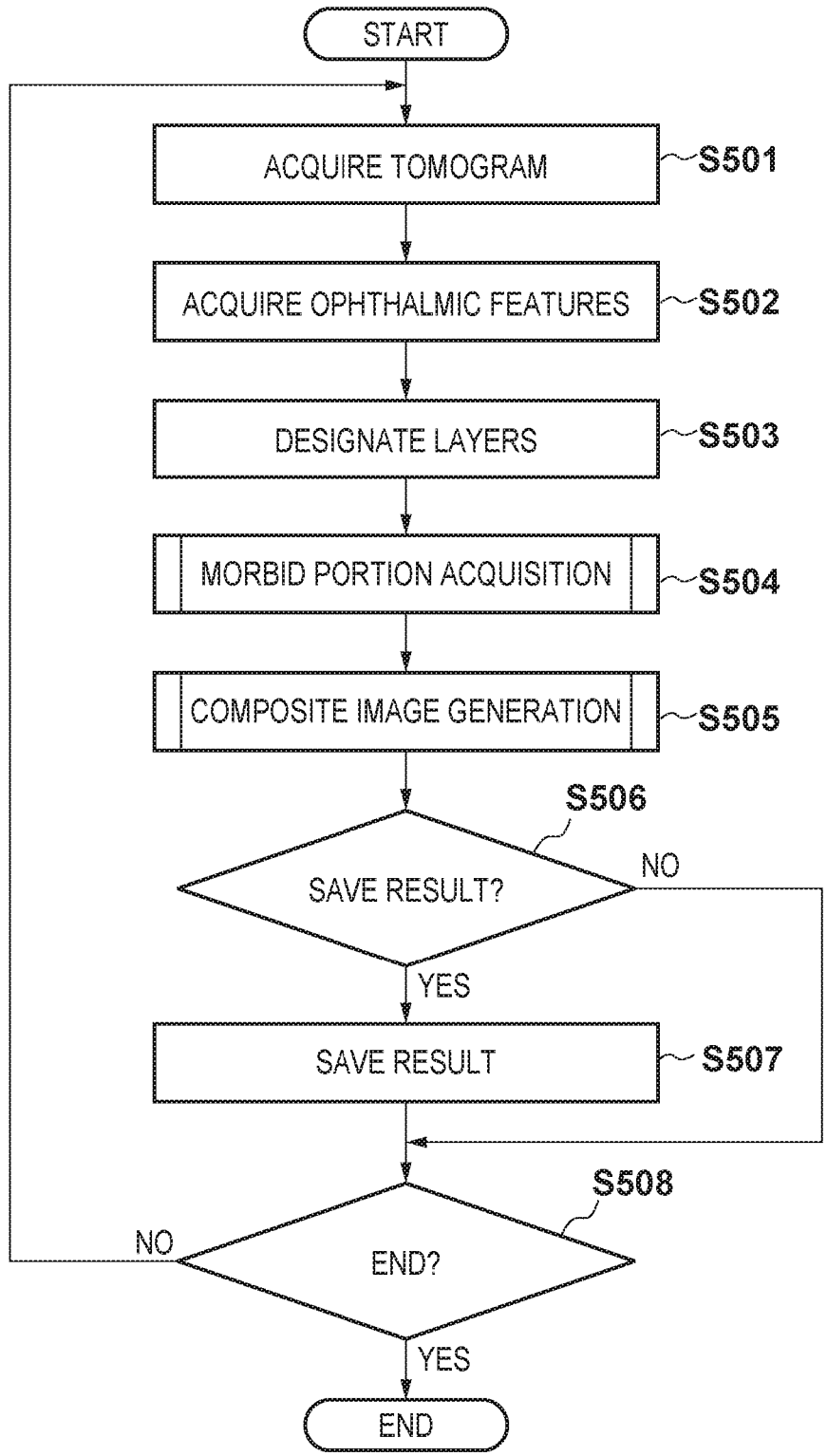
FIG. 5 is a flowchart showing the sequence of image processing in the image processing apparatus 100.

(1) Sequence of Overall Image Processing (FIG. 5)

In step S501, the tomogram acquisition unit 310 issues a tomogram acquisition request to the ophthalmic tomography apparatus 102 to acquire tomograms, and stores them in the storage unit 320. In step S502, the ophthalmic feature acquisition unit 331 acquires position information of ophthalmic features (inner limiting membrane B1, inner plexiform layer boundary B4, boundary B5 between inner and outer photoreceptor segments, retinal pigment epithelium boundary B6, and central fovea F1) from the tomograms stored in the storage unit 320.

In step S503, the layer designation unit 332 designates the types of layers according to the type of disease to be diagnosed. In step S504, the morbid portion acquisition unit 333 detects primary and associated morbid portions based on the position information of the ophthalmic features acquired by the ophthalmic feature acquisition unit 331 in step S502 and the types of layers designated by the layer designation unit 332 in step S503.

In step S505, the composite display unit 340 generates and displays a composite image using the primary and associated morbid portions detected in step S504. The instruction acquisition unit 350 determines in step S506 whether or not a save instruction required to save the image processing results in the data server 101 is acquired. If it is determined that the save instruction is acquired, the process advances to step S507.

In step S507, the image processing unit 330 and composite display unit 340 transmit the image processing results to the data server 101, and the process advances to step S508. On the other hand, if it is determined in step S506 that no save instruction is acquired, the process jumps to step S508.

The instruction acquisition unit 350 determines in step S508 whether or not an image processing end instruction is acquired. If it is determined that no end instruction is acquired, the process returns to step S501 to execute image processing for the next eye to be examined or (re-image processing for the same eye to be examined). On the other hand, if it is determined in step S508 that the image processing end instruction is acquired, the image processing ends.

Figure 6:
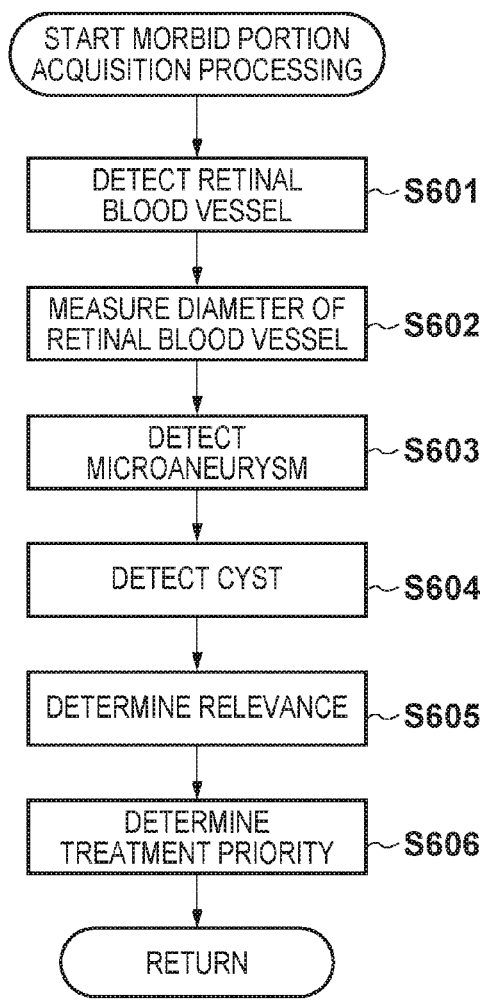
FIG. 6 is a flowchart showing the sequence of morbid portion acquisition processing in the image processing apparatus 100.

(2) Sequence of Morbid Portion Acquisition Processing (FIG. 6)

Details of the morbid portion acquisition processing (step S504) executed by the morbid portion acquisition unit 333 will be described below with reference to FIG. 6.

In step S601, the morbid portion acquisition unit 333 detects retinal blood vessels V from the retina inner layers P1 of the layers designated by the layer designation unit 332. More specifically, the morbid portion acquisition unit 333 generates a projection image by accumulating pixel values in a depth direction by limiting to the retina inner layers P1, and detects the retinal blood vessels V from the generated projection image using an arbitrary known line emphasis filter.

Note that the method of detecting the retinal blood vessels V from a two-dimensional projection image has been described. However, the blood vessel detection method is not limited to this. For example, after a region of interest (ROI) is set on the retina inner layers P1, retinal blood vessels V may be three-dimensionally detected without generating any projection image using a method described in a non-patent literature (K. Lee et al.; "3-D segmentation of retinal blood vessels in spectral-domain OCT volumes of the optic nerve head", Proceedings of SPIE Medical Imaging 2010, Vol. 7626, 76260V, 2010.)

In step S602, the morbid portion acquisition unit 333 measures the diameters of the retinal blood vessels detected in step S601. More specifically, the morbid portion acquisition unit 333 measures, as the diameters of the retinal blood vessels V, distances in directions perpendicular to the central axes of blood vessels obtained by converting retinal blood vessel regions into thin lines.

In step S603, the morbid portion acquisition unit 333 compares the diameters of the retinal blood vessels V measured in step S602 with a normal value of the diameter of a retinal blood vessel, which is read out in advance from the storage unit 320. If the measured diameter of each retinal blood vessel V is larger than the normal value by Tvd % or more, the morbid portion acquisition unit 333 determines it as a microaneurysm MAi (i=1, 2, . . . , n1), and stores a generation position (xi, yi) of that microaneurysm and a diameter Tdi of the retinal blood vessel V in the storage unit 320. Note that the diameter measurement method of the retinal blood vessels V is not limited to the method described above, and an arbitrary known measurement method may be used.

In step S604, the morbid portion acquisition unit 333 detects cysts Cj (j=1, 2, . . . , n2) from the retina outer layers P2 designated in step S503. More specifically, the morbid portion acquisition unit 333 generates a projection image by accumulating pixel values in a depth direction by limiting to the retina outer layers P2. Then, the morbid portion acquisition unit 333 labels pixels having luminance values Tg or less from the generated projection image, and detects low-luminance regions having areas Ta or more and degrees of circularity Tc or more as cysts Cj.

In step S604, the morbid portion acquisition unit 333 further detects areas Taj of the detected cysts Cj as information indicating the sizes of the associated morbid portions.

Note that the detection method of the cysts Cj is not limited to the method described above. For example, after a region of interest (ROI) is set on the retina outer layers P2, pixels having luminance values Tg or less may be labeled without generating any projection image, and low-luminance regions having volumes Tv or more and degrees of sphericity Ts or more may be detected as the cysts Cj. In this case, volumes Tvj are measured as information indicating the size of the cysts Cj.

Referring back to FIG. 6, in step S605, the relevance determination unit 333-1 measures distances LDi (distances between morbid portions) between the microaneurysms MAi acquired in step S603 and the cysts Cj detected in step S604. Furthermore, the relevance determination unit 333-1 determines, as combinations of primary and associated morbid portions, combinations (MAi, Cj) having shortest distances minLDi, which are equal to or smaller than a threshold (threshold=Tmin). In this case, a shortest distance of a microaneurysm MAi having no corresponding associated morbid portion is set to be 0.

In step S606, the treatability determination unit 333-2 calculates distances FDi between the microaneurysms MAi and central fovea F1, and sets "0" in treatable labels Li of microaneurysms MAi whose distances FDi are equal to or smaller than a predetermined distance (threshold=Tf). In this case, when a microaneurysm MAi exists in a region in which a treatment (laser irradiation) is allowed, "1" is set in Li; when it exists in a region where a treatment (laser irradiation) is not allowed, "0" is set in Li. Let n3 be the total number of microaneurysms MAi whose treatable labels Li are set to be "1".

Furthermore, in step S606, the treatment priority determination unit 333-3 calculates treatment priority levels Pi ($1 \leq i \leq n3$) for the microaneurysms MAi whose treatable labels Li are set to be "1". More specifically, the treatment priority determination unit 333-3 sorts the cysts Cj based on the areas Taj (or volumes Tvj) of the cysts Cj calculated in step S604 to set higher treatment priority levels Pi in descending order of Taj (Tvj).

Figure 7:
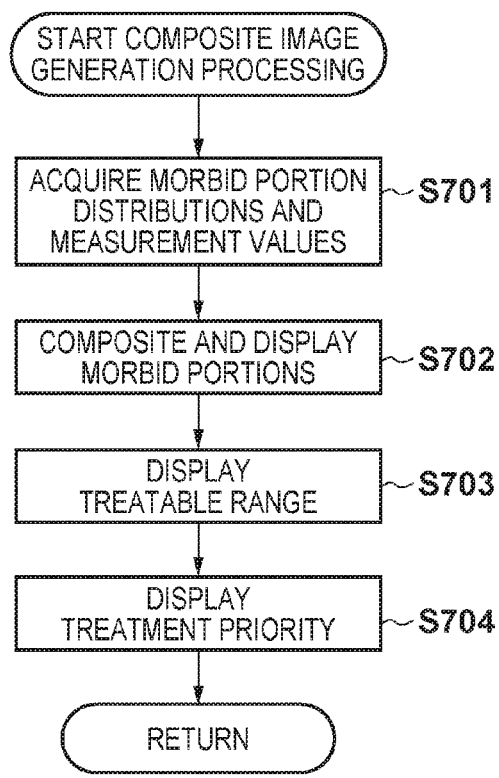
FIG. 7 is a flowchart showing the sequence of composite image generation processing in the image processing apparatus 100.

(3) Sequence of Composite Image Generation Processing (FIG. 7)

Details of the composite image generation processing (step S505) executed by the composite display unit 340 will be described below with reference to FIG. 7.

In step S701, the composite display unit 340 acquires, from the image processing unit 330, the position of the central fovea F1, the distributions of the retinal blood vessels V and microaneurysms MAi, the distribution of the cysts Cj, and values of the treatable labels Li and treatment priority levels Pi for the microaneurysms MAi.

In step S702, the image composition unit 341 superimposes the distributions of the retinal blood vessels V, microaneurysms MAi, and cysts Cj, the position of the central fovea F1, and a boundary of a treatable range (a circle having a diameter of 1 mm having the central fovea F1 as the center), which are acquired in step S701, on a predetermined fundus image generated from a tomogram. Also, the composite display unit 340 displays the generated composite image.

Also, the relevance display unit 342 displays combinations of primary morbid portions (microaneurysms MAi) and associated morbid portions (cysts Cj), which are determined to have relevance in step S605, in a mode which can identify relevance from each microaneurysm MAi to a corresponding cyst Cj. In this embodiment, arrows are displayed from the microaneurysms MAi to the cysts Cj on the composite image generated in step S702.

Note that the relevance display method is not limited to this, and an arbitrary method may be used as long as it can identify that morbid portions have relevance. For example, a frame which bounds a microaneurysm MAi and cyst Cj, which are determined to have relevance, may be displayed. Alternatively, only when the operator moves a mouse cursor to the vicinity of a microaneurysm MAi, information indicating relevance may be displayed.

In step S703, the treatability display unit 343 displays microaneurysms MAi having treatable labels Li=0 in a mode (color) different from the remaining microaneurysms based on the treatable labels Li of the microaneurysms MAi calculated in step S606. In this embodiment, the retinal blood vessels V and microaneurysms MAi having Li=1 are displayed in red, and microaneurysms MAi having Li=0 are displayed in gray.

Note that the treatability display mode is not limited to this. For example, X marks may be displayed beside the microaneurysms MAi having treatable labels Li=0. Alternatively, only when the operator moves a mouse cursor to the vicinity of a microaneurysm MAi, information indicating treatability may be displayed. Alternatively, microaneurysms MAi which are located near the boundary of the treatable range may be highlighted since careful examinations are required for them, and distances from the central fovea F1 may be displayed in the vicinity of the microaneurysms MAi.

In step S704, the treatment priority display unit 344 displays the treatment priority levels Pi calculated in step S606 on the composite image. In this embodiment, values of the treatment priority levels Pi are displayed in the vicinity of the microaneurysms MAi.

Note that the display mode of the treatment priority levels Pi is not limited to this. For example, treatment priority levels may be associated with color bars, and the microaneurysms MAi in the composite image may be displayed in colors indicating the treatment priority levels. Alternatively, only when the operator moves a mouse cursor to the vicinity of a microaneurysm MAi, information indicating a treatment priority level may be displayed. Alternatively, only treatment priority levels higher than a predetermined value Tp may be displayed on the composite image as information indicating the treatment priority levels.

<5. Example of Composite Image>

Figure 8:
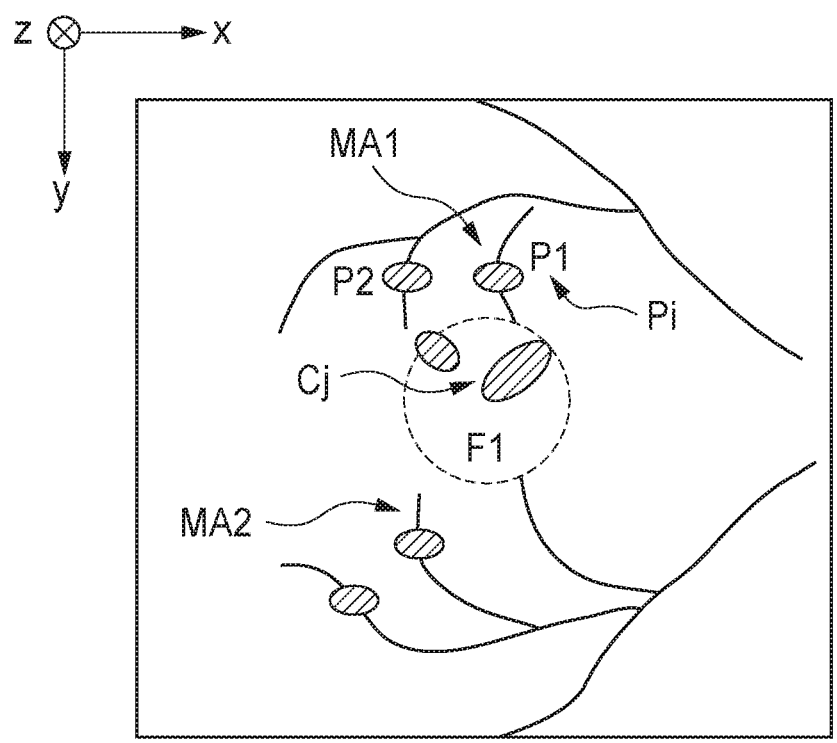
FIG. 8 shows an example of a composite image generated by the composite image generation processing in the image processing apparatus 100.

A composite image generated by the composite image generation processing in the image processing apparatus 100 will be described below. FIG. 8 shows an example of a composite image generated by the composite image generation processing in the image processing apparatus 100.

As shown in FIG. 8, a composite image generated by the image processing apparatus 100 composites and displays the primary morbid portions detected from the retina inner layers P1 and the associated morbid portions detected from the retina outer layers P2. With this image, the operator can easily recognize the presence/absence of leakage of plasma components from microaneurysms, priority levels of treatments for the primary morbid portions, and the like.

Also, since the position of the central fovea F1 is displayed at the same time, the operator can easily recognize whether or not each microaneurysm MAi is located within a laser treatable range (the advisability of treatments for the primary morbid portions).

As can be seen from the above description, the image processing apparatus 100 of this embodiment allows the operator to easily recognize the relevance between morbid portions which exist in a plurality of layers.

Second Embodiment

The first embodiment has explained the arrangement in which when a disease to be diagnosed is diabetic retinopathy, primary morbid portions are microaneurysms, and associated morbid portions are cysts, a composite image is generated for a predetermined tomogram. However, the present invention is not limited to this.

For example, when morbid portions exist in different portions (cell nuclei and axons) of cells which travel across a plurality of layers like glaucoma, it is important to allow an operator to easily recognize relevance between these morbid portions.

In this embodiment, in consideration of such characteristics of a disease such as glaucoma, a composite image, which composites an image indicating the thickness of a layer including cell nuclei of ganglion cells, an image indicating the thickness of a layer including axons, and an image indicating a nerve fiber distribution, is displayed. With this arrangement, the operator can easily recognize whether or not identical cells or tissues suffer morbid portions which exist in different layers.

A practical description will be given taking glaucoma as an example. In the case of glaucoma, since cell nuclei of ganglion cells exist in a ganglion cell layer L2 and axons exist in a nerve fiber layer L1 in general, disorders of cell nuclei of ganglion cells occur prior to those of axons in an early stage of the disease. For this reason, for example, when a thinned region of the nerve fiber layer L1 is detected, a region (ganglion cell layer L2) including cell nuclei of ganglion cells which travel in the thinned region also suffers from abnormality (thinning).

Hence, in this embodiment, when abnormality is detected by measuring tissue forms such as layer thicknesses from an ophthalmic tomogram, a composite image which superimposes images indicating a ganglion cell layer thickness distribution of a macular area, a nerve fiber layer thickness distribution of an optic papilla, and a nerve fiber distribution in an eye fundus is displayed. With this arrangement, the operator can easily confirm whether or not a nerve fiber which travels through a morbid portion (thinning of a layer) which exists in the nerve fiber layer L1 passes through that (thinning of a layer) in the ganglion cell layer L2. As a result, the operator can easily judge whether disorders of cell nuclei of ganglion cells are detected or noise components or the like are erroneously detected, thus improving reliability of morbid portion detection results.

An image processing apparatus 900 according to this embodiment will be described below focusing on differences from the image processing apparatus 100 according to the first embodiment.

Note that a case will be explained below wherein a disease to be diagnosed is glaucoma.

Also, in the following description, assume that the layer thicknesses of the ganglion cell layer L2 or statistical values (deviations) associated with differences between the layer thicknesses and a normal value are used as values which represent the degrees of disorders (thinning morbid portions) of cell nuclei of ganglion cells. However, the present invention is not limited to this, and GCC (Ganglion Cell Complex) layer thicknesses or deviations of the layer thicknesses may be used.

<1. Functional Arrangement of Image Processing Apparatus 900>

Figure 9:
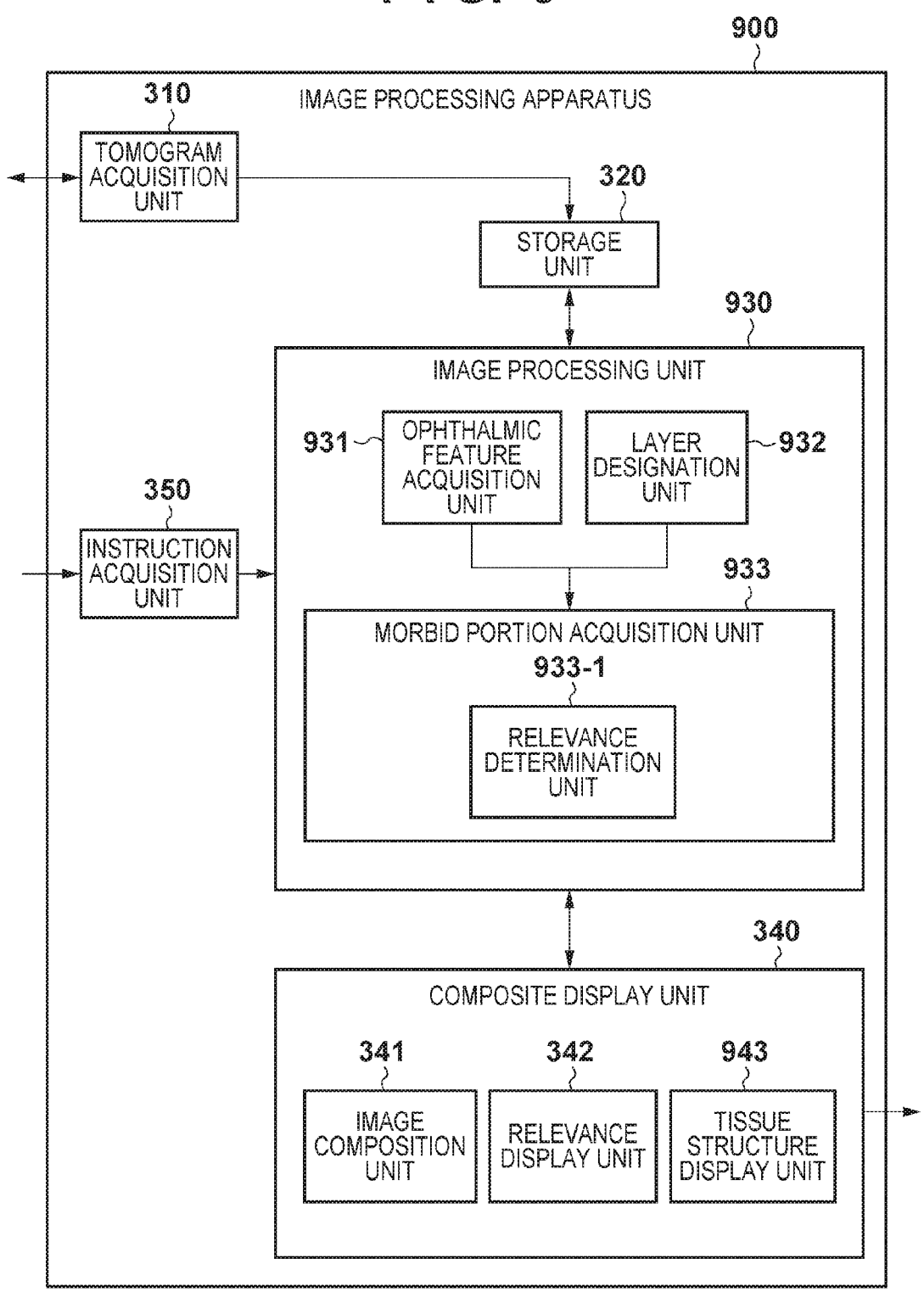
FIG. 9 is a block diagram showing the functional arrangement of an image processing apparatus 900 according to the second embodiment of the present invention.
Figure 10:
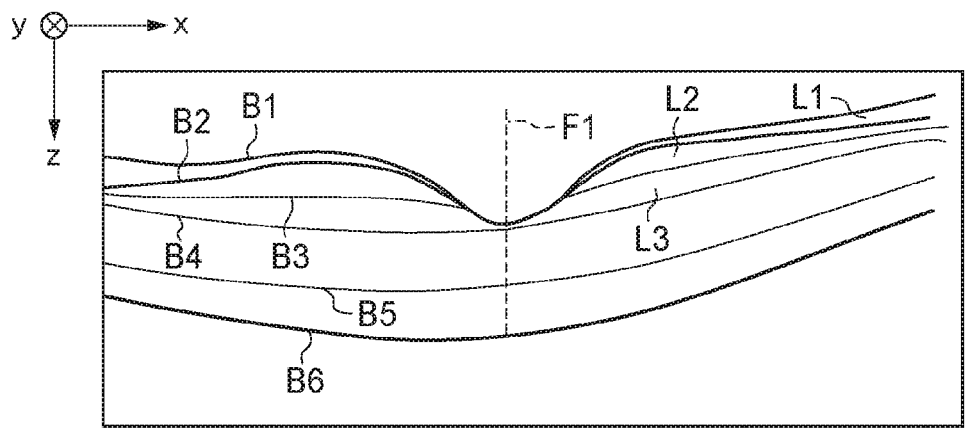
FIG. 10 shows an example of an ophthalmic tomogram used upon execution of an image processing function of the image processing apparatus 900.

The functional arrangement of the image processing apparatus 900 according to this embodiment will be described below with reference to FIGS. 9 and 10. FIG. 9 is a block diagram showing the functional arrangement of the image processing apparatus 900 according to this embodiment. FIG. 10 shows an example of an ophthalmic tomogram used upon execution of an image processing function of the image processing apparatus 900.

(1) Tomogram Acquisition Unit 310

A tomogram acquisition unit 310 transmits a tomogram acquisition request to an ophthalmic tomography apparatus 102. Note that tomograms to be acquired in this embodiment are those which include a macular area and optic papilla. The acquired tomograms are stored in a storage unit 320.

(2) Ophthalmic Feature Acquisition Unit 931

An ophthalmic feature acquisition unit 931 extracts, as ophthalmic features, an inner limiting membrane B1, nerve fiber layer boundary B2, ganglion cell layer boundary B3, inner plexiform layer boundary B4, boundary B5 between inner and outer photoreceptor segments, retinal pigment epithelium boundary B6, and central fovea F1 from the tomograms stored in the storage unit 320 (see FIG. 10).

Also, the ophthalmic feature acquisition unit 931 extracts the central position of an optic papilla D1 and the positions of end portions (RPE tips) of the retinal pigment epithelium boundary B6 in the optic papilla. Note that the positions of the end portions of the retinal pigment epithelium boundary B6 are calculated for respective B-scan images.

Note that the extraction method of the respective layer boundaries B1, B2, and B4 to B6, the central fovea F1, and the optic papilla D1 is the same as that described in the first embodiment. Hence, the extraction method of the ganglion cell layer boundary B3 will be describe below.

That is, after the nerve fiber layer boundary B2 and inner plexiform layer boundary B4 are acquired, local regions are set at respective points (x, y) in a region bounded by these boundaries to calculate variances of pixel values. Then, it is determined that a layer boundary exists in local regions with maximum variances, and these boundary positions are connected in the x- and y-axis directions, thereby extracting the ganglion cell layer boundary B3 (see FIG. 10). Note that the ophthalmic features extracted in this way are stored in the storage unit 320.

Furthermore, the ophthalmic feature acquisition unit 931 acquires, from the storage unit 320, pieces of information Nk (k=1, 2, . . . , n) indicating the distribution of ganglion cells in an eye fundus (the distribution of ganglion cells projected onto an x-y plane in FIG. 10). The pieces of distribution information of the ganglion cells in the eye fundus can be acquired from, for example, an SLO (Scanning Laser Opthalmoscope) image captured in a red-Free mode of an SLO. In this embodiment, assume that curves Nk (k=1, 2, . . . , n) indicating average nerve fibers generated based on SLO images obtained by capturing a plurality of healthy eyes in the red-Free mode are saved in advance in the storage unit 320.

Note that the nerve fiber distribution information acquisition method is not limited to this. For example, a surface image acquisition unit (not shown) may be included in the image processing apparatus 900, an SLO image (red-Free mode) of the same patient as the ophthalmic tomograms may be acquired from the surface image acquisition unit and may be stored in the storage unit 320. Then, the stored SLO image may be acquired.

(3) Layer Designation Unit 932

A layer designation unit 932 designates the nerve fiber layer L1 as a first layer and the ganglion cell layer L2 as a second layer. Note that the nerve fiber layer L1 is formed by gathering axons of the ganglion cell layer L2, and the ganglion cell layer L2 is formed by gathering cell nuclei of ganglion cells.

(4) Morbid Portion Acquisition Unit 933

A morbid portion acquisition unit 933 measures nerve fiber layer thicknesses and ganglion cell layer thicknesses based on the ophthalmic features acquired by the ophthalmic feature acquisition unit 931. Also, the morbid portion acquisition unit 933 detects thinned regions by comparing the measured nerve fiber layer thicknesses and ganglion cell layer thicknesses with their normal values. Furthermore, a relevance determination unit 933-1 determines relevance between the detected thinned regions and tissue structure (nerve fiber distribution) information acquired by the ophthalmic feature acquisition unit 931. Note that details of these processes by the morbid portion acquisition unit 933 will be described later.

(5) Composite Display Unit 940

A composite display unit 940 acquires the tissue structure (nerve fiber distribution) information, the layer thickness distribution of the nerve fiber layer L1, and that of the ganglion cell layer L2 from the morbid portion acquisition unit 933. Also, the composite display unit 940 acquires thinned regions NFi as morbid portions of the nerve fiber layer L1, thinned regions GCj as morbid portions of the ganglion cell layer L2, and detection reliabilities DRi of the respective thinned regions. Then, the composite display unit 940 generates a composite image for an SLO image using these pieces of information. Note that details of the composite image generation processing will be described later.

<2. Sequence of Image Processing in Image Processing Apparatus 900>

Figure 11:
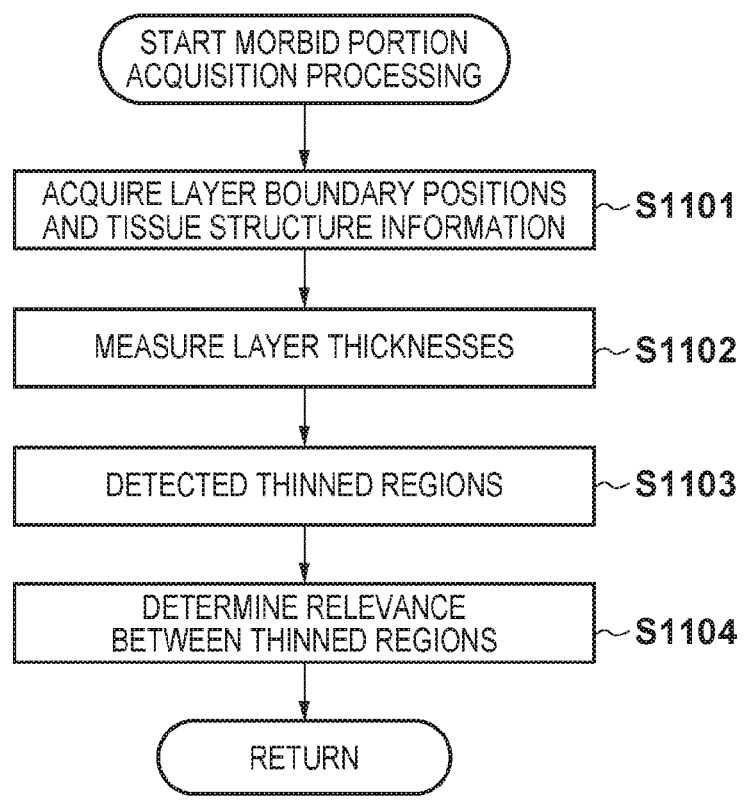
FIG. 11 is a flowchart showing the sequence of morbid portion acquisition processing in the image processing apparatus 900.

(1) Sequence of Morbid Portion Acquisition Processing (FIG. 11)

Details of morbid portion acquisition processing (step S504) executed by the morbid portion acquisition unit 933 will be described below with reference to FIG. 11.

In step S1101, the morbid portion acquisition unit 933 acquires the layer boundaries, the positions of the central fovea F1 and optic papilla D1, and tissue structure (nerve fiber distribution) information acquired by the ophthalmic feature acquisition unit 931, and normal values associated with respective layer thicknesses stored in the storage unit 320.

In step S1102, the morbid portion acquisition unit 933 measures nerve fiber layer thicknesses and ganglion cell layer thicknesses at respective points (x, y) in the eye fundus based on the layer boundaries acquired in step S1101. In this case, the morbid portion acquisition unit 933 does not measure nerve fiber layer thicknesses and ganglion cell layer thicknesses within the range of a diameter of 1 mm having the central fovea F1 as the center, and the interior of a Disc boundary of the optic papilla.

Note that in this embodiment, the position of the Disc boundary is set as follows. That is, lines Ai obtained by connecting end portions of the acquired retinal pigment epithelium boundary B6 in respective B-scan images (image numbers i) are calculated. Intersections E1$i$ and E2$i$ between the inner limiting membrane B1 and lines Ai' moved by a threshold Th toward the inner layer side in directions perpendicular to the lines Ai are calculated for respective B-scan images. Sets {E1$i$, E2$i$} of the obtained intersections are smoothly connected in an x-y plane to obtain the Disc boundary.

Referring back to FIG. 11, in step S1103, the morbid portion acquisition unit 933 compares the nerve fiber layer thicknesses and ganglion cell layer thicknesses with their normal values (values having given ranges). When the thicknesses are smaller than the normal values, corresponding regions are determined and detected as the thinned regions NFi of the nerve fiber layer L1 and the thinned regions GCj of the ganglion cell layer L2.

In step S1104, the relevance determination unit 933-1 determines relevance between the thinned regions NFi and GCj acquired by the morbid portion acquisition unit 933 based on the tissue structure (nerve fiber distribution) information acquired by the ophthalmic feature acquisition unit 931. That is, the relevance determination unit 933-1 determines whether or not the thinned regions NFi of the nerve fiber layer L1 and the thinned regions GCj of the ganglion cell layer L2 exist on an identical nerve fiber (on Nk).

At the time of determination, the coordinate system of the tissue structure (nerve fiber distribution) information Nk(x, y) and those of the morbid portion distributions NFi (x, y) and GCj (x, y) are aligned as follows. That is, since the positions of the central fovea F1 and optic papilla D1 are already calculated on the respective coordinate systems, translations (x, y) and rotation parameters for composite position alignment are calculated so that these two points are set at identical positions. Note that in this embodiment, since uniform image capturing conditions are adopted upon acquisition of SLO images and tomograms, the tissue structure information and morbid portion distributions are set in advance to have the same pixel size.

The morbid portion acquisition unit 933 further superimposes the tissue structure (nerve fiber distribution) information and morbid portion distributions based on the position alignment parameter values obtained as a result of position alignment.

Moreover, the morbid portion acquisition unit 933 calculates the thinned regions NFi of the nerve fibers layer L1 which exist on respective nerve fibers Nk. When the thinned regions NFi exist on the nerve fibers Nk, the morbid portion acquisition unit 933 checks whether or not the thinned region GCj exists on the same nerve fiber Nk. If the thinned region NFi of the nerve fiber layer L1 and the thinned region GCj of the ganglion cell layer L2 exist on the same nerve fiber Nk, an identical ganglion cell is more likely to have sustained damage. For this reason, the morbid portion acquisition unit 933 sets "1" in the detection reliability DRi of that thinned region NFi of the nerve fiber layer L1.

Note that the setting method of the detection reliability DRi of each thinned region NFi of the nerve fiber layer L1 is not limited to this. For example, in place of defining the reliability DRi by binary data (0 or 1), as described above, the reliability DRi may be defined by multi-valued data so as to be set to be higher in proportion to the number of travels Nk which pass through both the thinned regions NFi and GCj.

Figure 12:
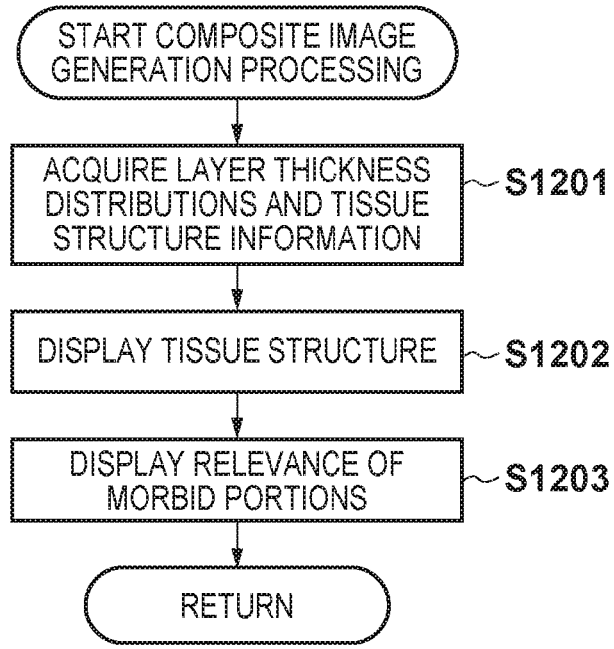
FIG. 12 is a flowchart showing the sequence of composite image generation processing in the image processing apparatus 900.

(2) Sequence of Composite Image Generation Processing (FIG. 12)

Details of the composite image generation processing (step S505) executed by the composite display unit 940 will be described below with reference to FIG. 12.

In step S1201, the composite display unit 940 acquires the tissue structure (nerve fiber distribution) information acquired in step S1101 and the layer thickness distributions of the nerve fiber layer L1 and ganglion cell layer L2 acquired in step S1102 from an image processing unit 930. Furthermore, the composite display unit 940 acquires the thinned regions NFi of the nerve fiber layer L1 and the thinned regions GCj of the ganglion cell layer L2 acquired in step S1103 and the detection reliabilities DRi of the thinned regions NFi acquired in step S1104 from the image processing unit 930.

In step S1202, a tissue structure display unit 943 displays the tissue structure (nerve fiber distribution) information acquired in step S1201 on a monitor 205.

In step S1203, an image composition unit 341 displays following pieces of information on the tissue structure (nerve fiber travel) information displayed in step S1202. That is, the image composition unit 341 translucently composites and displays a Deviation map of the nerve fiber layer thicknesses and the thinned regions NFi of the nerve fiber layer on a region of a diameter R1 having the optic papilla D1 as the center. Also, the image composition unit 341 translucently composites and displays a Deviation map of the ganglion cell layer thicknesses and the thinned regions GCj of the ganglion cell layer on the remaining region. Furthermore, the image composition unit 341 displays standard nerve fiber layer thickness measurement positions on the optic papilla (positions M1 on a circumference having a diameter of 3.45 mm having the optic papilla D1 as the center) as a reference.

Note that the composite display mode is not limited to this. For example, the detection reliabilities DRi of the thinned regions NFi acquired in step S1104 may be displayed in the vicinity of the thinned regions NFi on the displayed composite image. Alternatively, in place of displaying the tissue structure (nerve fiber distribution) information on the entire surface of the composite image, only nerve fibers Nk which pass through the thinned regions NFi or GCj may be displayed. Alternatively, in place of always displaying the tissue structure information and detection reliabilities DRi, they may be displayed at only a position designated by a mouse cursor.

<3. Example of Composite Image>

Figure 13:
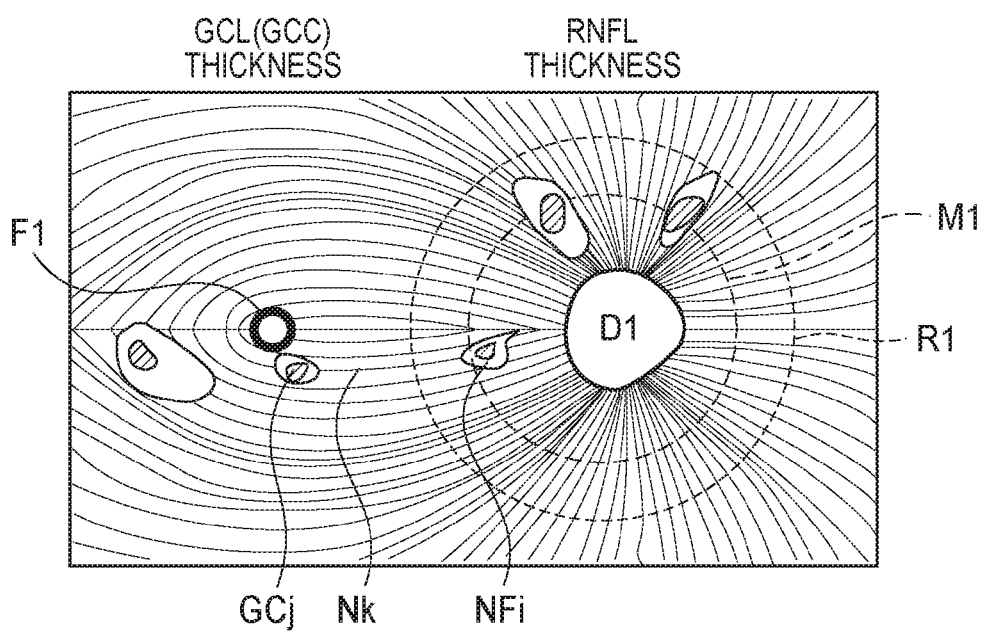
FIG. 13 shows an example of a composite image generated by the composite image generation processing in the image processing apparatus 900.
Figure 14:
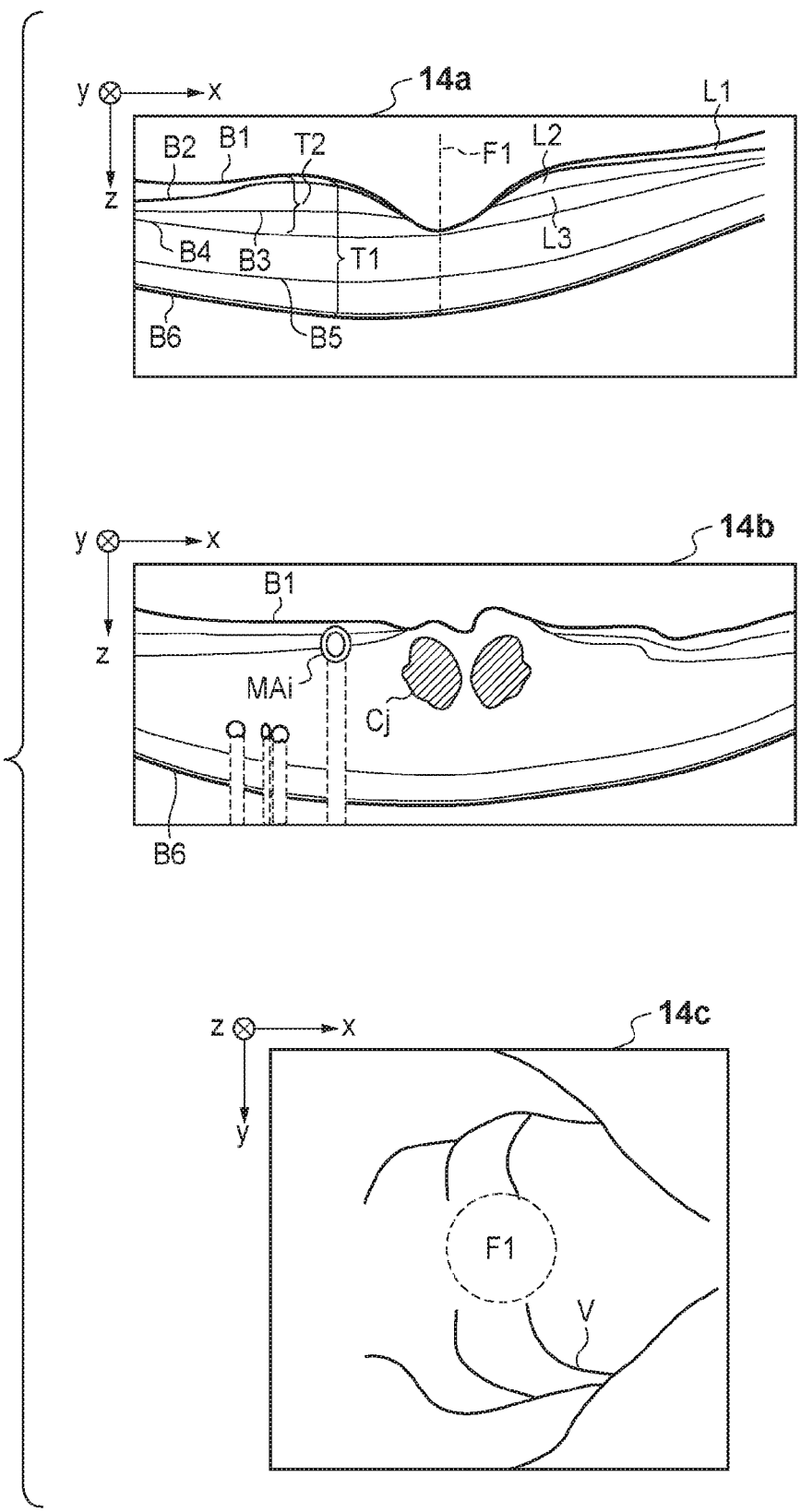
FIG. 14 shows states in which the boundaries of respective layers and blood vessels are detected, and the tissue forms of an eye portion are measured in various tomograms captured using an ophthalmic tomography apparatus.

A composite image generated by the composite image generation processing in the image processing apparatus 900 will be described below. FIG. 13 shows an example of a composite image generated by the composite image generation processing in the image processing apparatus 900.

As shown in FIG. 13, in a composite image generated by the image processing apparatus 900, the thinned regions of the ganglion cell layer L2 of the macular area and the thinned regions of the nerve fiber layer L1 of the optic papilla are composited and displayed on information indicating the nerve fiber distribution. With this display, the operator can easily recognize whether or not the thinned regions as morbid portions of glaucoma which exist in different layers correspond to identical cells or tissues.

As can be seen from the above description, the image processing apparatus 900 according to this embodiment allows the operator to easily recognize relevance between morbid portions which exist in a plurality of layers.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-259519 filed Nov. 19, 2010, which is hereby incorporated by reference herein in its entirety.

What is claimed is:

1. An image processing apparatus for processing a tomogram of an eye fundus, the apparatus comprising:
   a memory; and
   a processor that is in communication with the memory, the processor being configured to function as units comprising:
     (a) a feature acquisition unit configured to acquire anatomical features of the tomogram;
     (b) a morbid portion acquisition unit configured to detect a first morbid portion and a second morbid portion from a plurality of layers specified by the anatomical features acquired by said feature acquisition unit;
     (c) a determination unit configured to determine whether or not the first morbid portion and the second morbid portion exist on an identical tissue structure;
     (d) a generation unit configured to generate a composite image by projecting information of the tissue structure, the first morbid portion and the second morbid portion detected by said morbid portion acquisition unit, and a result determined by said determination unit onto a predetermined two-dimensional image; and (e) a display unit configured to display the composite image generated by said generation unit, wherein said determination unit determines whether or not the first morbid portion and the second morbid portion exist on an identical tissue structure in accordance with x,y-coordinate information of each of the first morbid portion and the second morbid portion.

2. The apparatus according to claim 1, wherein said morbid portion acquisition unit detects the first morbid portion and the second morbid portion by comparing nerve fiber layer thicknesses and ganglion cell layer thicknesses with their normal values.

3. The apparatus according to claim 2, wherein said display unit displays a circle indicating a position of a central fovea on the composite image.

4. The apparatus according to claim 3, wherein said determination unit further sets detection reliability of the first morbid portion based on a result determined by said determination unit.

5. The apparatus according to claim 1, wherein the first morbid portion and the second morbid portion correspond to a predetermined disease, and wherein the predetermined disease is glaucoma, the first morbid portion is a thinned region of a layer which exists in the nerve fiber layer, and the second morbid portion is a thinned region of a layer which exists in the ganglion cell layer.

6. The apparatus according to claim 1, wherein the information of the tissue structure includes information which indicates a nerve fiber distribution of the eye fundus, and wherein said display unit displays a nerve fiber distribution which passes through the first morbid portion and the second morbid portion on the two-dimensional image.

7. An image processing method for processing a tomogram of an eye fundus, the method comprising:

a feature acquisition step of acquiring anatomical features of the tomogram;

a morbid portion acquisition step of detecting a first morbid portion and a second morbid portion from a plurality of layers specified by the anatomical features acquired in the feature acquisition step;

a determination step of determining whether or not the first morbid portion and the second morbid portion exist on an identical tissue structure;

a generation step of generating a composite image by projecting information of the tissue structure, the first morbid portion and the second morbid portion detected in the morbid portion acquisition step, and a result determined in the determination step onto a predetermined two-dimensional image; and a display step of displaying the composite image generated in the generation step, wherein the determination step determines whether or not the first morbid portion and the second morbid portion exist on an identical tissue structure in accordance with x,y-coordinate information of each of the first morbid portion and the second morbid portion.

8. A non-transitory computer-readable storage medium including a program stored therein for executing an image processing method for processing a tomogram of an eye fundus, the image processing method comprising:

a feature acquisition step of acquiring anatomical features of the tomogram;

a morbid portion acquisition step of detecting a first morbid portion and a second morbid portion from a plurality of layers specified by the anatomical features acquired in the feature acquisition step;

a determination step of determining whether or not the first morbid portion and the second morbid portion exist on an identical tissue structure;

a generation step of generating a composite image by projecting information of the tissue structure, the first morbid portion and the second morbid portion detected in the morbid portion acquisition step, and a result determined in the determination step onto a predetermined two-dimensional image; and a display step of displaying the composite image generated in the generation step, wherein the determination step determines whether or not the first morbid portion and the second morbid portion exist on an identical tissue structure in accordance with x,y-coordinate information of each of the first morbid portion and the second morbid portion.

* * * * *